United States Patent [19]

Gubelmann-Bonneau

[11] Patent Number: 5,840,971

[45] Date of Patent: Nov. 24, 1998

[54] PROCESS FOR THE PRODUCTION OF ACETIC ACID BY CONTROLLED OXIDATION OF ETHANOL

[75] Inventor: Michel Gubelmann-Bonneau, Paris, France

[73] Assignee: Rhodia S.A., São Paulo, Brazil

[21] Appl. No.: 391,764

[22] Filed: Feb. 21, 1995

[30] Foreign Application Priority Data

Feb. 21, 1994 [FR] France ................................. 94 01923

[51] Int. Cl.$^6$ ................................................ C07C 51/235
[52] U.S. Cl. ............................................................ 562/538
[58] Field of Search ............................................. 562/538

[56] References Cited

U.S. PATENT DOCUMENTS 3,627,823  12/1971  Brockhaus et al. .

FOREIGN PATENT DOCUMENTS 0 294 846  12/1988  European Pat. Off. .

OTHER PUBLICATIONS

Studies in Surface Science and Catalysis vol. 72, Ruiz et al., "New Developments In Selective Oxidation By Heterogenous Catalysis", 1992 pp. 147–154.

The Catalytic Partial Oxidation of Ethyl Alcohol, Donald B. Keys, Nov. 1931, pp. 6 and 7.

*Primary Examiner*—Gary Geist
*Assistant Examiner*—Rosalynd Keys
*Attorney, Agent, or Firm*—Darby & Darby

[57] ABSTRACT

Disclosed herein is a process for the production of acetic acid by the controlled oxidation of ethanol. The process according to the invention comprises the reaction of ethanol with a source of oxygen. The reaction is performed in the presence of a catalyst in which the active stage is vanadium, titanium, and oxygen.

12 Claims, No Drawings

PROCESS FOR THE PRODUCTION OF ACETIC ACID BY CONTROLLED OXIDATION OF ETHANOL

FIELD OF THE INVENTION

This invention is related to a process for the production of acetic acid by controlled oxidation of ethanol, in the presence of a vanadium, titanium and oxygen based catalyst.

BACKGROUND OF THE INVENTION

The production of acetic acid from ethanol is a continuous method which is industrially exploited. Normally, there are two steps in the process. In the first one, a dehydrogenation reaction is performed with ethanol in a gaseous state, with the reaction performed on fixed bed of a copper and silicon based catalyst, at a temperature of between 250 and −300° C. It is also possible to perform an oxidizing dehydrogenation of the composition at 500° C., by passing it through a fixed bed of a silver based catalyst. In a second step, the acetaldehyde so obtained is transformed into acetic acid by oxidation under air, in a liquid state, at a temperature close to 60° C., and under 2.5 bar absolute pressure. The catalyst used in this second stage is cobalt and/or manganese based.

The disadvantage of such a process, beside the fact that it includes two steps, is that its normal yield ranges from 85 to 90%.

Another known process is one where the oxidation of ethanol into acetic acid is performed in one single step, using a heterogeneous palladium catalyst placed on a titanium, phosphorus and oxygen mixed composition. However, the selectivity in the formed acetic acid is not sufficiently high, and the productivity is too low. Finally, the synthesis of this catalyst is difficult.

The object of this invention is directed to a method for the synthesis of acetic acid based upon ethanol, for which the conversion rate of the alcohol and the selectivity in acetic acid are the highest possible, using a catalyst of simple composition and which is easy to prepare.

These as well as other purposes are achieved by this invention, which is related to a process for the preparation of acetic acid through the reaction, in gaseous state, of ethanol with a source of oxygen, in the presence of a catalyst, the active phase of which includes vanadium, titanium and oxygen.

It was observed that the catalyst used in the process of this invention allows for the practically quantitative transformation of ethanol, with a very great selectivity, to acetic acid. In addition, it was observed that the selectivity in the combustion products currently produced by the known processes is poor. Finally, as a direct consequence of the improved selectivity of said reaction, the quantity of by-products is decreased.

All such factors combined have resulted in the simplification of the subsequent separation of the acetic acid so produced.

In addition, the process, according to this invention, has the advantage of high yield, when compared with other known methods.

Another advantage of this invention is that the process is performed under average temperature and pressure conditions, which are simplified by the fact that the reaction may be performed in open air.

Finally, as it has already been mentioned, the catalysts used in the process of the invention are simple in their composition, do not contain any amount of noble metal and may be prepared by simple methods.

Other advantages and characteristics of this invention will become apparent to those of ordinary skill in the art by reading the description and from the examples submitted hereinbelow.

DETAILED DESCRIPTION OF THE INVENTION

For the purpose of convenience, the catalyst used in this invention is herein described below.

The active stage of the catalyst in question includes vanadium, titanium and oxygen.

In this specification, for reasons of convenience, the vanadium shall be designated by $V_2O_5$ and the proportions of said element shall be expressed with respect to said composition.

The quantity of vanadium in the active stage of the catalyst, expressed as $V_2O_5$, ranges from 0.1 to 30 weight %. It should be noted that concentrations outside these limits are not excluded, although they do not bring any additional advantages.

Following a preferred embodiment of the invention, the catalyst used in this invention includes an active stage, where the quantity of vanadium, expressed in $V_2O_5$, is from 0.2 to 15 weight %.

The titanium present in the active stage may be under any form of $TiO_2$ such as anatase, rutile, brookite or even bronze (indicated as (B)) or their mixtures. Preferably, the allotropic form of titanium oxide is selected from the group consisting of anatase, rutile forms or mixtures thereof.

The titanium oxide which enters the composition of the catalytic phase also presents, a specific surface, measured as per the B.E.T. method, from 1 to 150 $m^2/g$. More preferably, the specific surface is from 10 to 120 $m^2/g$.

The active stage of the catalyst used in this invention, may include at least one doping agent. The doping agent is selected amongst the following elements: Na, K, Rb, Cs, Mg, Ca, Sr, Ba, La, Zr, Nb, Cr, Mo, W, Mn, Re, Fe, Ru, Co, Ni, Pd, Cu, Ag, Zn, Cd, B, Al, Ga, In, Si, Ge, Sn, P, As, Sb, Ti and Bi.

In general, the quantity of doping element in the active phase ranges from 0.01 to 20 % atomic with respect to vanadium.

The active phase of the catalyst used in this invention may be achieved by any method already known in the art.

It is possible, as an example, to attempt to manufacture the active phase by mixing oxides of the constitutive elements of the active phase, or of compounds which may be transformed into oxides when taken to high temperatures. The mixture is then submitted to a calcination stage, eventually followed and/or preceded by a grinding of the mixture (chamotte technique).

Another convenient method for the preparation of the active phase consists of the following steps:

preparation of a mixture based on, at least, one of the constitutive elements of the active phase;

eventual precipitation of said elements;

drying of the treated mixture;

calcination of the dried product.

"Constitutive elements" are defined as not only vanadium and titanium, but the doping element(s) as well, added, if any, to the composition of the active phase. Generally, the constitutive elements are used in the form of a solution or a suspension.

In a preferred embodiment, the dispersant (or solvent) environment is water, however any other type of dispenser (or solvent) may be used. Other solvents for use include alcohols, such as methanol, ethanol, isopropanol and tert-butanol.

The constitutive elements of the active phase which enter the composition of the above mentioned mixture are used, in general, in the form of salts of inorganic or organic acids, or in the form of compounds, such as oxides and their by-products.

All acids or oxide by-products mentioned above are appropriate to the preparation of the mixture, provided they may be decomposed into the oxide of the corresponding element(s).

Non-limiting examples of such inorganic acids which may be used for the preparation of the above mentioned mixture include nitrates, sulfates, halogenates (which include one or more halogens), and ammonium salts.

Non-limiting examples of such organic acids or esters include formiates, oxalates, tartrates, acetates, acetylketonates and ethylhexanoates.

As mentioned above, it is also possible to use oxides or their by-products; these compounds may be used as particles or in soluble form especially with the addition of an acid or a base to the mixture.

Oxide by-products are defined herein as compounds of oxyhalogenates, alcoxides, aryloxides, and mainly the glycoxides type.

It should be noted that all compounds may be used either alone or as mixtures.

Examples of the compounds which contain vanadium and which are suitable to this preparation process, include, without limitation, vanadyl, ammonium metavanadate, vanadium oxyhalogenates such as $VOCl_3$, $(VO_2)Cl$, VOCL VOBr, $VOBr_2$, $VOF_3$, $VOF_2$, $VF_4$, $VBr_2$, $VI_2$, vanadyl acetylaketonate, vanadyl oxalate, metavanadic acid, vanadium hexacarbonyle, vanadium oxide tri-isopropoxyde, vanadium oxides, such as $V_2O_5$, $V_{7O13}$, VO, $VO_2$, $V_2O_3$, and $V_3O_7$.

Other titanium bearing compositions suitable for use in the present invention include $TiX_4$ type compounds, with X representing an halogen, preferably chlorine, and compounds of the $Ti(OR)_4$ type, with R representing a similar group and, more preferably, representing ethyl, isopropyl or di-butyl radicals.

Titanium oxide is also appropriate to this invention, under its different allotropic forms, mainly anastase, rutile, brookite or (B).

The compounds based upon a doping agent are selected from the group consisting of potassium chloride, potassium acetate, rubidium chlorides, niobium chloride or oxychloride, niobium oxalate, cesium sulfate, cesium acetate, iron sulfate, iron acetate, chrome chlorides or chlorates, chrome nitrates, chrome acetate, chrome acetylaketonate, ammonium dimolybdate, ammonium metatungstate and paratungstate, oxides and alkyloxides, such as zirconium ethoxide, silver oxide. Of course, this list should not be considered as a limiting one.

The temperature in which the mixing of the constitutive elements is made is normally between the temperature of 20° C. and the ebullition temperature of the selected dispersant or solvent.

In general, the concentration of the mixture ranges from 0.1 to 5M.

According to a first preferred embodiment, a precipitation step is then performed with respect to at least one of the constitutive elements present in the solution form. The elements may be precipitated, either simultaneously or successively. Normally, the precipitation occurs under agitation. All or part of them may be precipitated during such operation.

In this last case, the first and second stages are repeated as many times as necessary so that the dry product may contain all constitutive elements of the active phase, All compounds may be used as precipitant agents, as far as they combine with one or several constitutive elements, in the form of an insoluble compound in the selected medium. There the resulting insoluble compound enables to reach the oxide of the combined element(s).

It should be noted that the precipitation may be accomplished with one or more precipitant agents. Normally, the agent is selected from bases, such as the ammonium bases, or from inorganic or organic acids, such as hydrochloric acid or citric acid. It should be noted that water may constitute a convenient precipitant agent, for the application of this invention. It is quite clear that the selection of the precipitant agents is not limited to this list, which is only indicative, but not limiting.

The temperature under which the precipitation is preformed ranges from 20° C. to the ebullition temperature of the selected solvent.

Finally, the precipitation(s) stages may, if necessary, be followed by curing stages. These consist of leaving the precipitate in suspension, under agitation, for a period from 30 minutes to 4 hours. The curing temperature is within the temperatures mentioned previously.

The mixture which includes the constitutive elements of the active phase is dried, after having been passed through several precipitation steps.

A second embodiment of this process consists of drying the mixture as it is, in other words, without the previous precipitation step mentioned above.

Following a first variation, the drying operation is performed in two stages: in the first stage the solvent or dispersant of the mixture is evaporated till drying; and the second stage the sludge so obtained is dried. In general, the first stage is held at a temperature from 20° to 100° C. for the time necessary to obtain a flowing sludge.

The evaporation is normally accomplished under stirring. The resulting sludge is then dried, in a preferably non-reducing atmosphere, such as oxygen or air for an average time of 15 hours. The drying temperature is normally close to 120° C.

In accordance with a second variation, the drying is made by atomizing the solution or suspension, through any method known in the art. For this, the BUCHI type or the flash type atomizers, including but not limited to those claimed in the French applications for patents published under U.S. Pat. Nos. 2,257,326, 2,419,754, 2,431,321, are convenient for this process.

The atomization temperature is, normally, from 150° to 300° C.

The atmosphere under which the atomization is done is also non-reducing. Preferably, the atomization is performed under air, but the oxygen may be used for such a step.

The dried product, obtained as per any of the above mentioned variations, is then subjected to a calcination step. The calcination is done in the normal way, under a non-reducing atmosphere. Air is preferred for use in the step but oxygen may also be employed. The calcination temperature ranges normally from 200° to 1200° C. In general the duration of the operation ranges from 1 to 24 hours.

Before the calcination, the dried product may be submitted to a grinding step.

It should be noted that the calcinated product may eventually be submitted also, to such a treatment.

The catalyst used in the process of this invention may include, mainly, the above described active phase (massive form) or includes, also a diluting agent (dilute form).

In the special case where the catalyst includes a diluting (or supporting) agent, the active phase may be deposited on it, coated by it, or mixed with it.

The nature of the diluting agent is not critical, except that it should be inert with respect to the reagents in the selected reaction conditions.

Materials which may be used as catalyst support, include: silicium, alumine, silicium-alumine, clay, magnesium, magnesium silicate, diatomite. The types of support may be used in porous form or otherwise. Preferably, the support is in a non-porous form. If necessary, it is possible to enamel the support in order to make it non-porous.

Ceramic materials, such as cordierite, alumine, mullite, porcelain, silicium nitride, boron and silicium chlorides, may also be used as diluents.

The catalyst used in the process of the invention, whether diluted or not, is in the form of particles or of monolith. When the catalyst is in the form of particles, their granulometry value depends on the way the catalyst is used. Therefore it may vary, within wide limits, from a few microns to several millimeters. More preferably, and as an indication, a catalyst used on a fixed bed presents a granulometric division which in general ranges from 0.5 to 6 mm. The granulometry value of the particles of a given catalyst used in a fluid or mobile bed is normally from 5 to 700 microns and, preferably, it should contain 80% of the particles from 5 to 200 microns.

The quantity of the diluent which enters the composition of a catalyst ranges within wide limits, depending, on the way the catalyst is used. Therefore, the catalyst obtained by coating or deposition of the active phase on the support show an amount of active phase which ranges normally from 0.1 to 30%, preferably from 2 to 20% by weight of the total weight of the finished catalyst (active phase plus support).

If the catalyst includes a support dispersed in the active phase, the quantity of active phase should be from 1 to 90% by weight of the total weight of the finished catalyst.

According to a given embodiment of the invention, the reaction is held in the presence of a catalyst of the coated type.

The final catalyst, in accordance with this invention, may be obtained as per any classic method known in the art.

Therefore, the massive catalysts, which include essentially the active phase, such as defined above, may be formed by extrusion, molding, grinding, crushing or other action of the active phase or of its previous form, in order to produce a monolith or particles of convenient granulometry.

Here, as well as in the remaining portion of this specification, the previous form of the active phase, is defined as the mixture of the elements which constitute this phase, in all steps prior to the calcination described before.

In the case of catalysts which include a diluent, the above mentioned means may be used. Therefore, it is possible to mix the active phase with the required proportion of the diluent and, as an example, to extrude or to mold the resulting mixture.

However, other methods may also be applied. Following a first configuration, the diluent is put in contact, preferably in the form of rough particles, with the active phase or its previous form, in a blender with high shearing (LODIGE type devices) or in a granulation device (pelletizing machine, in the form of a drum or plate). The operation is held, in general, under a temperature between 20° and 150° C., for a period of time which is necessary to the coating of the support by a desired quantity of the active phase, preferably in open air and for at least 30 minutes. The particles so obtained are normally calcinated at a temperature which ranges from 300° to 500° C., preferably from 450° to 500° C. The calcination stages lasts, in general, at least 3 hours.

A second possible method for the manufacture of the catalyst consists of using the impregnation technique. In accordance with this technique, the support is impregnated with a suspension of the active phase or with a suspension or solution of its previous form.

The impregnation step is followed by a drying step, normally at a temperature from 100° to 200° C., in open air and for at least 30 minutes. It is possible then to return to the impregnation-drying cycle and finish it by a calcination step in open air.

The calcination temperature ranges from 400° to 600° C., and the process lasts for many hours.

A possible variant consists of making a calcination step between the impregnation drying steps.

Following a third method of preparation for the catalyst, to the mixture of at least one of the elements which constitute the active phase are added the support, preferably formed as particles. The mixture thus formed is then treated under the different methods of the process for the preparation of the catalytic phase, as described above, namely, the eventual precipitation, the drying and the calcination steps.

Of course, such methods of preparation are given only as examples and should not be interpreted as a limiting listing.

As mentioned before, this invention is related to a process for the preparation of acetic acid through the reaction in the gas phase, of ethanol with an oxygen source, in the presence of a catalyst as previously defined.

There are no special conditions relative to the quality of the ethanol used in the process. However, for the purposes relative to the separation of the formed acid, the use of ethanol with a minimum 90% purity is preferred. Technical ethanol, that which has a low percentage content of water, is appropriate, for the purpose of this invention.

The controlled oxidation reaction of ethanol is performed in the presence of an oxygen source. It may be on an oxygen basis, either pure or diluted in an inert gas, such as helium, argon or nitrogen.

According to a preferred embodiment for the present invention, the oxidation reaction uses air with a low content of oxygen as the source of oxygen. For air with a low content of oxygen, essentially an oxygen and nitrogen mixture, in which the content of oxygen is lower than 20% may be used.

According to a preferred method of the present invention, the molar proportion between oxygen and ethanol is from 0.5 to 10.

A variation of the process consists of the use of a gas mixture which includes water amongst other constitutes. The composition of the gas mixture, with ethanol being the source of oxygen and water, may change within wide limits.

Except if otherwise mentioned hereinbelow, all percentage values are expressed in total mol number of the gas mixture.

In a general way, the content of ethanol in the gas mixture ranges from 0.5 to 20%. Preferably, the ethanol content shall be from 2 to 15%.

The oxygen content in the gas mixture broadly ranges from 0.5 to 20% and preferably ranges from 2 to 20%.

The content of water in the gas mixture in question ranges broadly from 0 to 40% and preferably from 0 to 20%.

According to a preferred embodiment, the molar proportion of water/ethanol in the mixture is from 0.5 to 10. The complement, to 100%, is constituted by the inert gas mentioned before.

The gas mixture is then put in contact with the catalyst, according with the invention.

The device in which the method of the present invention is performed is part of the classic devices for catalytic reactions in gas phase and may be used in a continuous or discontinuous process.

Therefore, it is possible to perform the reaction in the presence of a catalyst in a fixed, fluid or vehicle type catalyst.

The operational temperature ranges, in general, from 100° to 300° C, preferably from 120° to 250° C.

The total pressure of the reaction gas mixture ranges from 0.5 to 3 bars absolute pressure.

The feeding flow of the reacting agents, with respect to the value of the catalytic bed, ranges from 100 to 10000 $h^{-1}$.

The separation of the formed acetic acid is considerably simplified with respect to the classic processes. Actually, the mixture which leaves the reactor has practically no ethanol, due to the quasi quantitative conversion of the alcohol. As a consequence, the separation of the acid consists only of the separation of the acid from the gas by-products and water. As with the later separation of the acetic acid and water, it may be mainly performed by the liquid extraction.

The present invention is further described below in working examples which are intended to exemplify the invention without limiting its scope.

EXAMPLES

In the following examples, the performance of the catalysts are computed as follows:

ethanol conversion (% mol)

$$\text{Ethanol conversion} = \frac{(\text{Mol number of fed ethanol} - \text{mol number of produced ethanol})}{(\text{mol number of fed ethanol})} \times 100$$

oxygen conversion (% mol)

$$O_2 \text{ conversion} = \frac{(\text{Mol number of } O_2 - \text{mol number of } O_2 \text{ produced})}{(\text{mol number of fed } O_2)} \times 100$$

selectivity of a product X (acetic acid, combustion products)(% mol)

$$\text{Selected } X = \frac{\text{mol number of ethanol converted into } X}{(\text{mol number of fed ethanol} - \text{mol number of produced ethanol})} \times 100$$

Example I

Preparation of the $V_2O_5$, $TiO_2$/clay catalyst 90 g of $TiO_2$ (1.125 mol), with a BET surface equal to 100 $m^2/g$ (sold by Rhône-Poulenc), were placed in a pelletizer machine and dry impregnated by 200 $cm^3$ of a vanadyl oxalate solution.

The solution used included 28.89 g of dihydrate oxalic acid (229.26 mmol) and 12.86 g of commercial grade of JANSSEN $V_2O_5$ (70.6 mmol) in water.

The product so obtained was calcinated in open air at 500° C. for 3 hours.

The composition of the calcinated product contained 12.5% by weight of $V_2O_5$ and a 0.126 V/Ti rate.

25 g of the active phase so prepared were placed on 100 g of clay pellets, with 5 mm mean diameter (sold by Rhône-Poulenc) by the coating method, with the aid of a glucose aqueous solution.

The product was then calcinated, on air, at 500° C. for 3 hours.

The final content of the catalyst, in active phase, was 17.96% by weight.

Example 2

Use of the catalyst

This example shows the application of the above mentioned catalyst for the preparation of acetic acid from ethanol.

The catalyst (20 $cm^3$) was introduced in an INOX (stainless) continuous reactor and on a fixed bed, equipped with a fluid sand heating bed and two chromatographs on line, one operating with an ionization flame detector, and the other operating with a heat conduction meter detector.

The gas feeding was controlled by the massive flow meters.

The ethanol and the water were under liquid form and fed by a dosing pump (HPLC, GILSON).

The feeding flow (expressed in mol %) was constituted by:

ethanol/$O_2$/$H_2O$/$N_2$–2.5/3/5/89.5

The volume flow, per hour, was 3,200 $h^{-1}$.

The reactor pressure was kept constant at 1.7 bar absolute pressure.

The performances were as follows:

| | |
|---|---|
| Conversion: | |
| ethanol: | 92% |
| Selectivity: | |
| Acetic acid: | 97% |
| Combustion products: | 3% |
| Acetic Acid Yield: | 194 g/h/l. |

Example 3

Use of the catalyst

The same process of the example above was used, with the following operational conditions:

The feeding flow (expressed in % mol) was constituted by:

ethanol/$O_2$/$H_2O$/$N_2$=2.5/18/5/5/74

The volume flow, per hour, was 6,400 $h^{-1}$.

The reactor pressure was kept constant at 1.7 bar absolute pressure and the operational temperature was 185° C.

The operational temperature was 200° C. The performances were as follows:

| | |
|---|---|
| Conversion: | |
| ethanol: | 87% |
| Selectivity: | |
| Acetic acid: | 96% |
| Combustion products: | 4% |
| Acetic Acid Yield: | 356 g/h/l. |

What is claimed:

1. A process for the production of acetic acid by the reaction of gaseous ethanol with a source of oxygen comprising the steps of:

contacting said gaseous ethanol with said source of oxygen in the presence of a vanadium, titanium and oxygen based catalyst in an amount of $V_{20}O_5$ between about 0.1 and 30% by weight of the total weight of the finished catalyst and at least one doping agent present in an amount of 0.01 to 20% atomic weight in relation to the vanadium, said source of oxygen being atmospheric air present in an amount between about 0.5 and 20% molar based on the gaseous mixture, submitting said gaseous mixture of ethanol and atmospheric air to a pressure of about 0.5 to 3.0 bar, and recovering said acetic acid, wherein said process has selectivity of acetic acid of about 96 to 97% and conversion of ethanol of about 87 to 92%.

2. The process of claim 1 wherein said catalyst contains an amount of $V_2O_5$ in the range of between 0,2 and 15% by weight of said catalyst.

3. The process of claim 1 wherein said doping agent is selected from the group consisting of Na, K, Rb, Cs, Mg, Ca, Sr, Ba, La, Zr, Nb, Cr, Mo, W, Mn, Re, Fe, Ru, Co, Ni, Pd, Cu, Ag, Zn, Cd, B, Al, Ga, In, Ti, Si, Ge, Sn, P, As, Sb, and Bi.

4. The process of claim 1 wherein said gaseous ethanol is a gaseous mixture comprising from 0,5 to 20% molar of ethanol.

5. The process of claim 4 wherein said gaseous mixture is from 2 to 15% molar of ethanol.

6. The process of claim 1 wherein said gaseous mixture comprises between 2 and 20% molar of oxygen.

7. The process of claims 1, 4, 5, or 6, wherein said gaseous mixture has an oxygen/ethanol molar ratio between 0,5 and 10.

8. The process of claim 28 wherein said gaseous mixture also comprises 0 to 40% moles of water.

9. The process of claim 8 wherein said gaseous mixture comprises 2 to 20% in moles of water.

10. The process of claim 9 wherein the water/ethanol ratio is between 0,5 and 1 0.

11. The process of claim 1 wherein said gaseous mixture comprises a diluting gas selected from the inert gases or nitrogen.

12. The process of claim 1 where the reaction is started at a temperature of between 120° C. and 250° C.

* * * * *